United States Patent [19]

Ebina

[11] Patent Number: 5,143,727
[45] Date of Patent: Sep. 1, 1992

[54] METHOD FOR PREVENTING DIARRHEA

[75] Inventor: Takusaburo Ebina, Sendai, Japan

[73] Assignees: Sendai Institute of Microbiology, Sendai; Mitsubishi Kasei Corporation, Tokyo, both of Japan

[21] Appl. No.: 239,003

[22] Filed: Aug. 29, 1988

Related U.S. Application Data

[63] Continuation of Ser. No. 473,750, Mar. 9, 1983, abandoned, which is a continuation-in-part of Ser. No. 255,808, Apr. 20, 1981, abandoned.

[30] Foreign Application Priority Data

Aug. 29, 1980 [JP] Japan .................. 55-119312

[51] Int. Cl.$^5$ .................. A61K 39/12; A61K 39/42
[52] U.S. Cl. .................. 424/89; 424/85.8; 424/86
[58] Field of Search .................. 424/85.8, 86, 89

[56] References Cited

U.S. PATENT DOCUMENTS 4,341,763 7/1982 Zygraich .................. 424/89

OTHER PUBLICATIONS

Ebina, The Lancet (Oct. 29, 1985) pp. 1029-1030.
Ebina, Med. Microbiol Immunol (1985) 174:177-185.
Bridger et al., Infection and Immunity, vol. 31, No. 3, pp. 906-910, Mar. 1981.
The Merck Manual, 10th Edition, Merck Sharp and Dohme Research Laboratories, published, pp. 1101-1105, 1961.
Cecil Textbook of Medicine, Wyngaarden & Smith, ed., W. B. Sanders Co., publishers, pp. 2109-2112, 1982, 16th ed.

Primary Examiner—Johnnie R. Brown
Assistant Examiner—Abdel A. Mohamed
Attorney, Agent, or Firm—Oblon, Spivak, McClelland, Maier & Neustadt

[57] ABSTRACT

A therapeutic agent which is milk collected from a milk animal which has been immunized by a virus or viruses capable of growing in the digestive tract can be used to prevent a disease such as intractable diseases including multiple sclerosis, acute gastroenteritis and viral hepatitis, which are caused by said virus.

5 Claims, 1 Drawing Sheet

METHOD FOR PREVENTING DIARRHEA

This application is a continuation of application Ser. No. 06/473,750, filed on Mar. 9, 1983, now abandoned, which is a continuation-in-part of Ser. No. 06/255,808 filed Apr. 20, 1981, now abandoned.

BACKGROUND OF THE INVENTION

1. Field of the Invention

The present invention relates to a therapeutic method, more particularly, to a therapeutic method for diseases such as intractable diseases including multiple sclerosis, acute gastroenteritis, viral hepatitis and the like, which are caused by virus capable of growing in the digestive tract.

2. Description of the Prior Art

Heretofore, no effective preventive method has been found for intractable neuropathic diseases such as multiple sclerosis, Bechet disease, myasthenia gravis, amyotrophic lateral sclerosis, systemic lupus erythematosus, Parkinson disease, and slow virus infection disease. Corticosteroids such as Prednisolone are only examples which have been practically used. However, they are accompanied by strong side effects.

SUMMARY OF THE INVENTION

As a result of a long term virological and immunological study on the above-described diseases, it has now been found that these intractable diseases are autoimmune diseases triggered by virus infections and, to prevent such diseases, it is only necessary to avoid the growth of respective virus in a digestive tract. It has also been found that, when a milk animal such as cow or goat, preferably in her pregnancy, is immunized by viruses, lots of anti-virus antibody are contained in the milk, particularly, colostrum and, upon oral administration of the milk such intractable disease or diseases can be considerably prevented.

DESCRIPTION OF THE PREFERRED EMBODIMENTS

Figure 1:
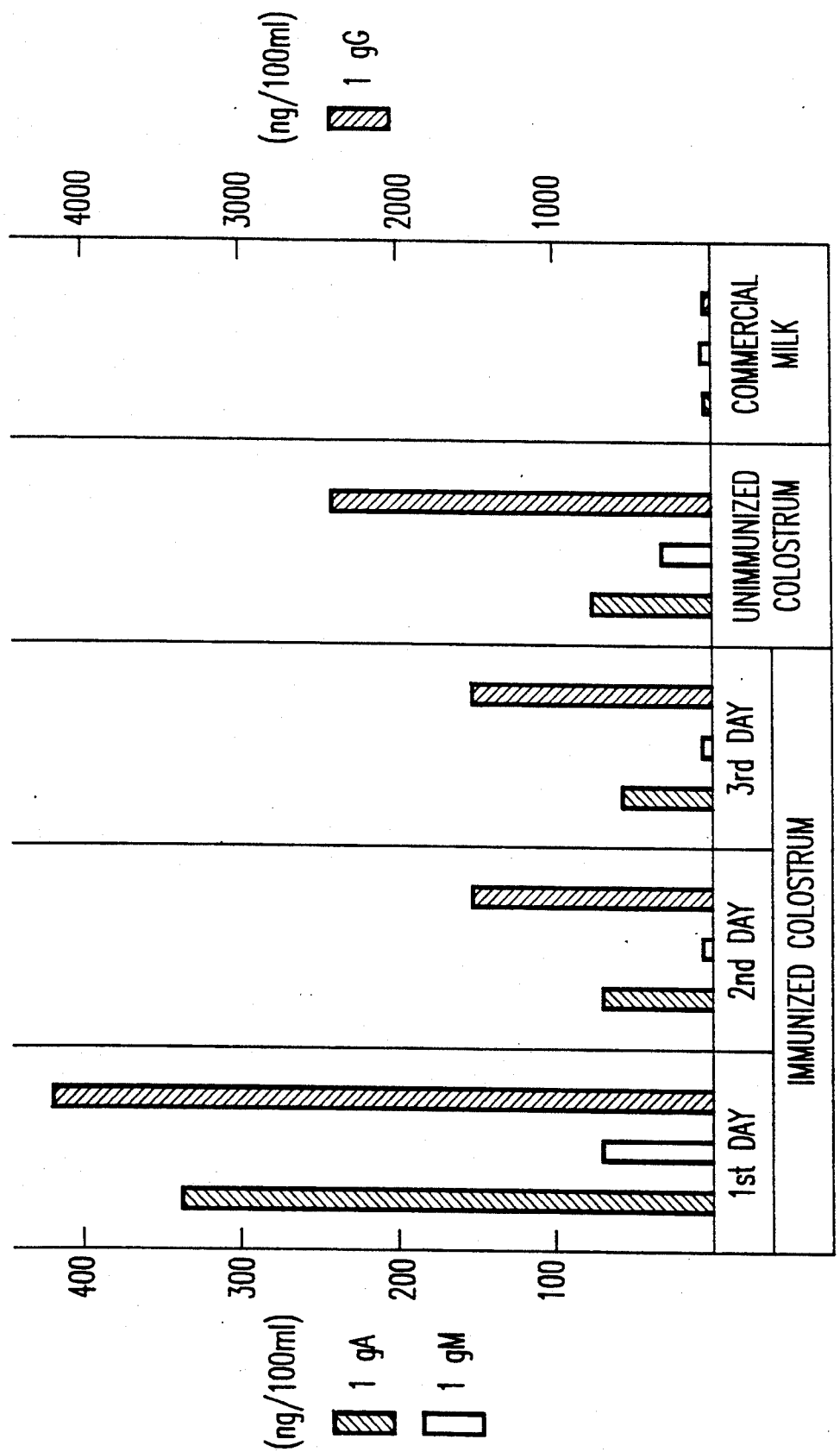
FIG. 1 shows the amounts of IgA, IgM and IgG contained in a therapeutic agent for intractable diseases according to this invention.

A therapeutic agent according to this invention and adapted for the prevention of such intractable diseases may be produced, for example, as follows:

An immunization of a milk animal in her 6th-9th month pregnancy is carried out by subcutaneously or intramuscularly inoculating the same animal with virus or virus vaccine every 7 to 14 days and 3 to 6 times in total. The amount of virus or virus vaccine to be inoculated is not specifically limited but its upper limit is determined depending upon side effects which may be caused by the inoculation. As virus vaccine, vaccine of measlesvirus or distempervirus may be employed. Colostrum is collected, preferably, for 1 to 3 days after the birth, to provide a therapeutic agent for the above-described diseases.

Similarly, a therapeutic agent for infantile acute gastro-enteritis can be produced by an inoculation of virus such as rotavirus, adenovirus, calicivirus, astrovirus, coronavirus, minireovirus, or parvovirus. On the other hand, a therapeutic agent for viral hepatitis can be prepared by an inoculation of A-type, B-type or Non-A and Non-B type hepatitisvirus. It is also possible to use vaccine in place of virus per se.

Milk of a milk animal according to this invention and providing an effect to prevent a disease caused by virus may be applied in any suitable manner, but an oral administration is preferred as it permits intestinal absorption. Thus, the milk is orally administered as it is or after converting it to powder milk through dehydration.

The dosage administered will be dependent upon the age, condition and weight of the patient, the state of the disease, kind of concurrent treatment if any, frequency of treatment, and the nature of the effect desired. Generally, a daily dosage measured as milk will be from about 0.1-10 ml per kg of body weight. Normally, from 1-2 ml per kg per day, in one or more applications per day is effective to obtain the desired result.

The active ingredient of the milk of this invention can be employed in dosage forms such as tablets, capsules, powder packets, granules, or liquid solutions, suspension, or elixirs, for oral administration.

Besides the active ingredient of this invention, the composition will contain a solid or liquid non-toxic pharmaceutical carrier for the active ingredient. In one embodiment of a composition, the solid carrier can be a capsule of the ordinary gelatin type.

In another embodiment, the active ingredient can be tableted with or without adjuvants, or put into powder packets.

The present invention will be further illustrated in the following examples:

EXAMPLE 1

A Holstein cow in her 8th-month pregnancy was inoculated subcutaneously with 10 ampoules of attenuated measeles vaccine (Schwarz strain) and 5 ampoules of distemper vaccine (Onderstepoort strain) every 10 days and 5 times in total. After birth, colostrum was collected on each of the first, second and third days. Each colostrum (20 l) thus obtained was subjected to centrifugation at 5,000 rpm for 20 minutes to remove bacteria and fat therefrom. Its supernatant was collected as skim milk. The measles-neutralizing antibody titer of the colostrum obtained on each of the first, second and third days is given in Table 1.

TABLE 1

|  | Day of milk collection | Measles-neutralizing antibody titer |
|---|---|---|
| Immunized Colostrum | 1st day | $2^4$ |
|  | 2nd day | 2 |
|  | 3rd day | <2 |
| Unimmunized colostrum | 1st day | <2 |
| Commercial milk |  | <2 |

The IgA, IgG and IgM of the colostrum obtained on each of the first, second and third days after the birth are shown in FIG. 1.

EXAMPLE 2

Colostrum obtained on the first day after the birth of a pregnant cow in a manner similar to that followed in Example 1 was orally administered every morning to four patients affected by multiple sclerosis at a daily dosage of 100 ml for 30 days (1 course). As a control, two patients affected by the same disease were orally administered similarly with the colostrum obtained on the first day after the birth of a pregnant, unimmunized Holstein cow. Results are shown in Table 2 (the patient group administered with a therapeutic agent according to this invention) and Table 3 (control).

TABLE 2

(Patient Group Administered with A Therapeutic Agent According to This Invention)

| Initials of patient, age | Symptoms before and after administration | | Judgement |
|---|---|---|---|
| | Before | After | |
| S. R. 25 years old | Abasia, deteriorated impressibility, double vision, spastic paralysis of limbs, accelerated reflex of limb tendons, pathologic reflex (+), cerebellar syndrome (+), emotional incontinence (+), dysuria (+). | After the first course, abasia and emotional incontinence improved, but progressed again after the stop of administration. Improved again in the second course. | Apparently effective |
| I. A. 42 years old | Dullness of the lower limbs, headache, progressed hypesthesia of Th 2 or less and paresthesia, incomplete spastic paralysis of all limbs, epileptic reflex of left body (+), dysuria. | After the first course, dysuria improved but progressed again after the stop of administration. In the second course, dysuria and numbness of the lower limbs improved. | Apparently effective |
| N. K. 36 years old | Paresthesia below chest, hypesthesia of Th 6 or less, remarkable progress of vibration sensation of both lower limbs, weakened muscle power of both lower limbs. | Remarkable improvement to the sensation, particularly, vibration sensation, after the first course. | Effective |
| E. K. 30 years old | Abasia, numbness of lower limbs, forearms, hands and fingers, progressed sensation particularly vibration sensation, of both lower limbs, accelerated reflex of lower limb tendons, pathologic reflex (+), pollakiuria. | No change observed after first course of administration. | Unchanged |

TABLE 3

(Control)

| Initials of patient, age | Symtoms before and after administration | | Judgement |
|---|---|---|---|
| | Before | After | |
| K. C. 37 years old | Abasia, incontinence of urine, paresthesia of Th 6 or less, hypesthesia, paresthesia of both upper limbs, progressed deep sensation, accelerated reflex of upper and lower limb tendons, cerebellar syndrome (+). | After the first course of administration, paresthesia improved. But, painful convulsion developed at upper left limb. | Ineffective |
| T. T. 46 years old | Tingle feeling at both fingers and heels, spastic limb paralysis, pathologic reflex (+) at both sides, paresthesia below knees of both lower limbs, hypesthesia of upper left limb. | No improvement observed after the first course of administration. | Unchanged |

As apparent from the above experiments, a therapeutic agent for intractable diseases of the present invention does not develop side effects and is effective to cure such intractable diseases by its oral administration of about 100 ml a day.

EXAMPLE 3

A Holstein cow in her 8th-month pregnancy was inoculated subcutaneously with $10^9$/ml of human rotavirus (wa strain) every 10 days and 5 times in total. After birth, colostrum was collected on each of the first, second and third days. Each colostrum (10 l) thus obtained was subjected to centrifugation at 7,000 rpm for 30 minutes to remove bacteria and fat therefrom. Its supernatant was collected as skim milk. The human rotavirus-neutralizing antibody titer of the colostrum obtained on each of the first, second and third days is given in Table 4.

TABLE 4

|  | Day of milk collection | Human rotavirus-neutralizing antibody titer |
|---|---|---|
| Immunized colostrum | 1st day | 5,120 |
|  | 2nd day | 320 |
|  | 3rd day | <160 |
| Unimmunized colostrum | 1st day | <2 |

EXAMPLE 4

Colostrum obtained on the first day after the birth of a pregnant cow in a manner similar to that followed in Example 3 was orally administered every morning to seven 6-month to 5-year old children at a daily dosage of 20 ml for 15 to 30 days. As a control, seven other children were orally administered similarly with the colostrum obtained on the first day after the birth of a pregnant, unimmunized Holstein cow.

All of seven children administered with the colostrum of the unimmunized Holstein cow were affected by infantile acute gastroenteritis. On the other hand, of seven children administered with immunized colostrum, only one was affected by infantile acute gastroenteritis.

As apparent from the above experiment, a preventive therapeutic agent for infantile acute gastroenteritis of the present invention is effective to prevent such infantile acute gastroenteritis by its oral administration.

Having now fully described the invention, it will be apparent to one of ordinary skill in the art that many changes and modifications can be made thereto without departing from the spirit of the invention as set forth herein.

What is claimed as new and intended to be covered by Letters Patent is:

1. A method for preventing diarrhea in man caused by human rotavirus, comprising:
    administering to a person a therapeutically effective amount of milk or ingredients thereof collected from a milk producing animal immunized with human rotavirus.
2. The method of claim 1, wherein the virus is in the form of a viral vaccine.
3. The method of claim 1, wherein the milk producing animal has been immunized with the virus or a vaccine of the same virus while in her pregnancy.
4. The method of claim 1, wherein the milk is colostrum.
5. The method of claim 1, wherein the milk producing animal is a cow.

* * * * *